United States Patent [19]

Krause-Hooyman

[11] Patent Number: 4,626,502

[45] Date of Patent: Dec. 2, 1986

[54] METHOD FOR EXPOSING BACTERIAL ANTIGEN IN BACTERIAL CELLS ASSAY USING SAME

[75] Inventor: Laurel Krause-Hooyman, Deerfield, Ill.

[73] Assignee: Abbott Laboratories, North Chicago, Ill.

[21] Appl. No.: 574,779

[22] Filed: Jan. 27, 1984

[51] Int. Cl.⁴ .................. G01N 33/53; C12Q 1/38; C12Q 1/14

[52] U.S. Cl. .................................... 435/7; 435/23; 435/36

[58] Field of Search ................................ 435/7, 23, 36

[56] References Cited

PUBLICATIONS

Masaki, T., et al., BBA, vol. 660, (1981), pp. 44–50.

*Primary Examiner*—Christine M. Nucker
*Assistant Examiner*—Stephen C. Wieder

[57] ABSTRACT

The use of achromopeptidase to expose bacterial antigen in an improved assay for the antigen in a test sample is disclosed.

1 Claim, No Drawings

METHOD FOR EXPOSING BACTERIAL ANTIGEN IN BACTERIAL CELLS ASSAY USING SAME

TECHNICAL FIELD

This invention relates to bacterial lysis methods, and more particularly to diagnostic assays including such lysis methods for the exposure or release of bacterial antigen contained in the bacteria prior to performing an assay for the antigen.

BACKGROUND ART

Organisms classified as gram positive bacteria, for example, *Streptococcus pyogenes*, are known to be pathogenic in humans. Such organisms are the causative agents in Strep throat and have been implicated in complications such as post-streptococcal glomerulonephritis and rheumatic fever. Accordingly, prompt diagnosis and treatment of infections caused by these organisms is imperative in medical practice.

*Streptococcus pyogenes*, in particular, possesses a group of antigens consisting of a carbohydrate (rhamnose and N-acetyl-glucosamine) bound to the peptidoglycan of the cell wall, and are classified on this basis as Group A Strep. Diagnostic assays for detecting Group A strep can therefore be designed to rely upon the ability of antibody generated in animals to detect the Group A carbohydrate antigen. Since much of this antigen is internal to the organism, exposure of the antigen by mechanical, chemical or enzymatic means aids in increasing the sensitivity of the assays. Conventionally, the carbohydrate antigen has been extracted chemically from whole cells or cell walls by hot formamide, autoclaving in the presence pf HCl (Rantz-Randall method) or through the generation of nitrous acid. Enzymatic release of the antigen has been effected through the use of enzymes from the soil microorganisms of species Streptomyces, e.g., *Streptomyces albus, Streptomyces globesporus*, and *Streptomyces griseus*, as well as through the use of proteolytic enzymes like trypsin.

SUMMARIZATION OF THE INVENTION

It has been discovered that the enzyme achromopeptidase can be used to effectively and inexpensively expose or release antigens specific for various strains of intact organisms, such as the group A carbohydrate of Group A Strep organisms. When such exposure is carried out as part of an assay for detecting the antigen, the necessity for culturing cells is eliminated and the assay can be performed more rapidly and inexpensively by comparison with conventional assays which do not utilize this enzyme. The present invention is based upon this discovery and involves an improvement in an assay for determining a bacterial antigen in a test sample comprising antigen-containing bacterial cells. The improvement comprises exposing bacterial antigen in the cells by contacting them with achromopeptidase prior to performing the assay. The improvement provides a rapid, single and less expensive method for exposing the antigen by comparison with known techniques.

DETAILED DESCRIPTION OF THE INVENTION

An enzyme preparation called achromopeptidase (TBL-1), prepared from the organism *Achromobacter lyticus* M497-1, was used in the following Example, which is intended to be merely illustrative of the present invention and in no way constitutes a limitation thereon.

It has been recognized that *Achromobacter lyticus* M497-1 produces three kinds of alkaline proteases (protease I, II, and III) in culture as well as two bacteriolytic enzymes (see Japanese Pat. No. 71 42953). A lytic enzyme preparation of TBL-1 is known to be bacteriolytic for gram-positive organisms and has been used to isolate cell walls.

EXAMPLE

An experiment was conducted to test the bacteriolytic capabilities of Achromopeptidase in the presence of Group A strep. Group A strep (Type T-12) was resuspended in 0.01 Molar (M) Tris buffer, pH 8, containing 0.01M NaCl at a concentration of $1 \times 10^8$ bacteria/milliliter (ml). Achromopeptidase (WAKO, No. LTR 9868) was initially added to 2 ml aliquots of this bacterial solution (final concentration of enzyme was 500 units/ml). The aliquots were incubated for various lengths of time at 37° C. and the decrease in optical density at 630 nanometers (nm) at each time was monitored. After 15 minutes a drop in optical density (OD) of 75% was observed, indicating lysis of cells. After 60 minutes, complete clearing was noted. In addition, exposure and/or release of antigen into the supernatant was shown by the ability of rabbit anti-Group A strep antiserum to precipitate antigen in a subsequent capillary precipitin test.

The nature of the antigen exposed to the supernatant was further studied by the following experiments. First, approximately 200 grams (g) of Group A strep, Type T12, was resuspended in 1 liter of 0.01M Tris HCl with 0.01M NaCl, pH 8. To this suspension, 0.67 g achromopeptidase (1000 units/mg) was added and The mixture stirred at 37° C. for three days. The cell walls were then centrifuged down and the supernatant concentrated and dialyzed utilizing an Amicon filter (YM 10). Five milliliters of the concentrated supernatant were diluted 1:2 in Tris buffer (0.05M) and placed on a 75 ml DEAE column equilibrated in the Tris buffer, pH 8. The column was washed with buffer and a linear salt gradient (to 1M NaCl in buffer) was applied. Two ml fractions were collected and the OD was monitored at 280 nm. All fractions were tested for their ability to react with antiserum to Group A strep. Two main antigen peaks were eluted from the DEAE column; the first peak was neutral (or basic) at pH 8, eluting in the wash, and the second peak was weakly acidic, eluting shortly after the application of the linear gradient. Both peaks contained rhamnose as analyzed by the methylpentose assay as well as some protein as assessed by the Lowry protein assay. Immunoelectrophoresis of these fractions confirmed their antigenicity and charge.

Next, the achromopeptidase preparation containing both neutral and acidic antigen was fractionated on a G-100 Sephadex column to determine the molecular weight of the antigens. One ml of sample was placed on a column with a bed-volume of 115 ml. The column was equilibrated in 0.1M ammonium carbonate buffer (pH 7.3) and the sample was eluted with the same buffer at a flow rate of 12 ml/hr. Two ml fractions were then collected and tested for the presence of antigen. The OD of the eluent was also monitored at 280 nm. Only one broad molecular weight of antigens was observed (estimated to be approximately 36,000 daltons) eluting near the center of the peak. Thus, it appears that the antigens exposed by achromopeptidase from Group A strep consist primarily of two charged species (neutral or basic at pH 8 and acidic) with molecular weights close to 36,000.

It was of interest to determine if the antigens exposed by treatment with achromopeptidase were indeed antigenically related to the carbohydrate which defines strep as Group A. Therefore, the achromopeptidase preparations were compared to Group A polysaccharide (APS) prepared by the following procedures: HCl extraction, according to the Rantz-Randall method, treatment with mutanolysin (from Streptomyces globisporus) and nitrous acid extraction. An Ouchterlony double diffusion analysis was carried out on these preparations by placing appropriate samples of each in outer wells of an agarose slide and placing antistrep Group A antiserum in the center well. The results of the double diffusion analysis indicate that there is antigenic identity between the single lines of the HCl and nitrous acid extracts. These lines appeared to fuse with two lines associated with the mutanolysin and achromopeptidase extracts. However, slight spurring indicating partial identity appeared between the inner line of diluted achromopeptidase preparation and the nitrous acid preparation. Since identical spurring did not occur between the achromopeptidase preparation and any other preparation, it is difficult to interpret this result. Double diffusion analysis of the two antigens eluted from the DEAE column indicated antigenic identity with HCl-Extracted APS. Therefore, it can be stated that achromopeptidase does release the group antigen of *Streptococcus pyogenes*.

Finally, the use of achromopeptidase (TBL-1) in accordance with the invention to expose antigen in assays designed to detect and diagnose Group A strep was demonstrated. A commercial immunoassay kit containing latex coated with specific antibody to Group A strep (Streptex, Burroughs-Wellcome) was utilized. Strep Group A grown on blood agar plates was placed in either extracting enzyme (*Streptomyces griseus* extract) provided by the manufacturer of achromopeptidase. The organisms were incubated for one hour at 37° C. and then the samples were tested according to the manufacturer's instructions. A positive result from this assay test was noted for samples containing Strep Group A treated with either *Streptomyces griseus* extract or achromopeptidase, indicating the efficacy of achromopeptidase not only as a bacteriolytic agent against Strep Group A, but also to expose the antigen which defines bacteria as Strep Group A, and thus demonstrating the ability of this enzyme to function as part of an assay system for such bacterial antigens.

It will thus be apparent to those skilled in the art that achromopeptidase can be advantageously used in many different types of assays known in the art which are designed for the diagnosis of Strep Group A and other antigens, for example, agglutination assays, hemagglutination assays or enzyme-linked immunoassays. It is to be appreciated that this enzyme can therefore be used to expose or release antigens which are specfic for various strains of bacteria, yeasts and other organisms, providing a rapid means for identifying such organisms in various noncultural types of assays.

The amount of achromopeptidase used in the invention to expose bacterial antigen is not critical, and can vary widely, depending upon the type of bacteria and amount thereof in the test sample. In the usual case, upon contact with small amounts of achromopeptidase, bacterial cells in a test sample have been found to rapidly release their bacterial antigens together with other cell contents into the test sample. Furthermore, achromopeptidase used in accordance with the present invention has been shown to be capable of effective use in exposing or releasing antigen found in bacterial cells at a wide range of pH values, from slightly acidic to basic. However, it is preferred that it be used in a pH range of from about 8 to about 9.5.

It has been found that the use of surfactants, solvents, buffers and other agents (in combination with lytic agents), conventionally used in typical lytic techniques which are carried out prior to performance of conventional assays to release cell contents, are totally unnecessary in the practice of the present invention. Accordingly, this invention not only eliminates cell culturing, but also provides a means of exposing antigen contained within bacterial cells more simply, easily, rapidly and inexpensively than known techniques so that the antigen can be efficiently detected by conventional assays.

Various modifications of this invention as specifically described herein will be apparent to those skilled in the art. All such modifications are intended to be within the spirit and scope of this invention, which is limited solely as defined in the following claims.

What is claimed is:

1. A diagnostic immunoassay for Strep Group A bacteria the improvement comprising:
   treating a test sample of antigen-containing bacterial cells with achromopeptidase thereby exposing Strep Group A antigen and, then detecting said antigen by using Strep Group A antibody in an immunoassay format.

* * * * *